United States Patent
Deutz et al.

[11] Patent Number: 6,129,770
[45] Date of Patent: Oct. 10, 2000

[54] HAIR DYE AGENTS WITH AT LEAST ONE CONDITIONER

[75] Inventors: Herbert Deutz, Kall; Mustafa Akram, Hamburg; Astrid Kleen, Duesseldorf, all of Germany

[73] Assignee: Henkel Kommanditgesellschaft auf Aktien (KGaA), Duesseldorf, Germany

[21] Appl. No.: 08/981,735

[22] PCT Filed: Jun. 7, 1996

[86] PCT No.: PCT/EP96/02482

§ 371 Date: Jun. 29, 1998

§ 102(e) Date: Jun. 29, 1998

[87] PCT Pub. No.: WO97/01323

PCT Pub. Date: Jan. 16, 1997

[30] Foreign Application Priority Data

Jun. 26, 1995 [DE] Germany .......................... 195 22 569
May 2, 1996 [DE] Germany .......................... 196 17 490

[51] Int. Cl.$^7$ ........................................ A61K 7/13
[52] U.S. Cl. .................... 8/406; 8/405; 8/407; 8/597
[58] Field of Search ...................... 8/405, 406, 407, 8/408, 409, 410, 411, 412, 414, 415, 426, 602, 597

[56] References Cited

U.S. PATENT DOCUMENTS

| | | | |
|---|---|---|---|
| 3,993,436 | 11/1976 | Fujinuma ........................ | 8/424 |
| 4,268,264 | 5/1981 | Grollier et al. ................. | 8/410 |
| 4,479,803 | 10/1984 | Bachmann et al. ............. | 8/406 |
| 4,620,850 | 11/1986 | Bachmann et al. ............. | 8/406 |
| 4,746,322 | 5/1988 | Herlihy ........................... | 8/405 |
| 5,494,489 | 2/1996 | Akram et al. ................... | 8/408 |
| 5,611,817 | 3/1997 | Moeller et al. .................. | 8/405 |

FOREIGN PATENT DOCUMENTS 0 026 473  4/1981  European Pat. Off. .

(List continued on next page.)

OTHER PUBLICATIONS

English language translation of JP 56–77220, Hoyu Co, pp. 1–8, Jun. 1981.

(List continued on next page.)

*Primary Examiner*—Caroline D. Liott
*Attorney, Agent, or Firm*—Wayne C. Jaeschke; Glenn E.J. Murphy

[57] ABSTRACT

A hair treatment formulation for coloring human hair comprising a substantive dye or oxidation dye precursors and a hair care agent comprising a compound of the formula (I):

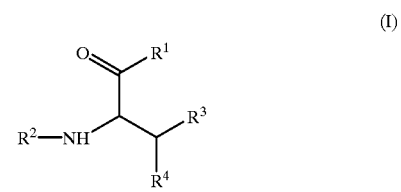

wherein $R^1$ is hydroxy, $C_1$ to $C_3$ alkoxy, or a group of the formula (II):

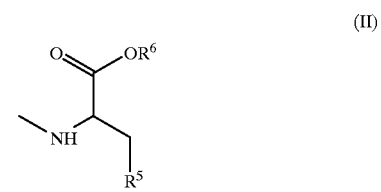

wherein $R^2$ is hydrogen or $C_1$ to $C_3$ alkyl, $R^3$ is hydrogen or methyl, $R^4$ is hydroxy, $-(CH_2)_3-NH_2$, 4-hydroxyphenyl, or $H_2PO_3$, $R^5$ is hydroxy, $-CH_2)_3-NH_2$, or 4-hydroxyphenyl, and $R^6$ is hydrogen or $C_1$ to $C_3$ alkyl, including physiologically compatible salts of organic or inorganic bases of said compounds of formula (I). The coloring formulations according to the invention condition and improve the structure of hair, eliminating the need for the usual post-coloring treatments.

2 Claims, 3 Drawing Sheets

FOREIGN PATENT DOCUMENTS

| | | |
|---|---|---|
| 3 929 333 | 3/1991 | Germany . |
| 41 36 997 | 5/1993 | Germany . |
| 4335624 | 4/1995 | Germany . |
| 4335628 | 4/1995 | Germany . |
| 44 08 506 | 9/1995 | Germany . |
| 50-10385 | 4/1975 | Japan . |
| 56-77220 | 6/1981 | Japan . |
| 59-106413 | 6/1984 | Japan . |
| 60-78915 | 5/1985 | Japan . |
| 6-263621 | 9/1994 | Japan . |
| 6-271434 | 9/1994 | Japan . |
| 7-330559 | 12/1995 | Japan . |
| 8-20518 | 1/1996 | Japan . |
| WO93/19725 | 10/1993 | WIPO . |

OTHER PUBLICATIONS

Kosmetik by Wilfried Umbach, George Thieme Verlag, Stuttgart, p 284–291, 297 (1988).

Cosmetics Science and Technology, Editor Edward Sagarin, Interscience Publishers, Inc., New York, 479–530 (1957).

Grundlagen und Rezepturen der Kosmetika, 2nd edition, Hüthig Buch Verlag, Heidelberg, p 782–815 (1989).

"Hair Coloring", Rev. Prog. Coloration, vol. 15: 52–65 (1985).

J.F. Corbett, The Chemistry of Synthetic Dyes, vol. 5, edited by Venkataraman, Academic Press, New York, 475–534 (1971).

Parfümerie & Kosmetik, 75:755–58 (1994).

SÖFW Journal, 121:367–72 (1995).

Proc. Inst. Mech. Eng., London, 35–102 (1899).

Textile Res. J. 30:800–801 (May, 1963).

Textile Res. J. 33:465–471 (Jun., 1963).

Proc. Int. Wool Textile Res. Conf. Cirtel, Paris, 4:487–493 (1965).

Kolloid–Zeitschrift und Zeitschrift für Polymere 216/217:277–286 (1967).

Colloid and Polymer Sci., 265:965–970 (1987).

Mell. Text. 68:923–926 (Dec. 1987).

Textile Res. J. 37: 898–907 (1967).

Proc. 7th Int. Wool Text Res. Conf., Tokyo vol. I:283–292 (1985).

Proc. 6th Int. Wool Text Res. Conf., Pretoria, vol. V:235–266 (1980).

J. Appl. Polymer Sci. 48:137–150 (1993).

H. Deutz, Doktorarbeit, RWTH Aachen (1993).

HAIR DYE AGENTS WITH AT LEAST ONE CONDITIONER

BACKGROUND OF THE INVENTION

1. Field of the Invention

This invention relates to hair treatment formulations in the form of colorants for human hair based on substantive dyes and/or oxidation dye precursors and containing standard cosmetic ingredients and at least one hair-care agent.

2. Discussion of the Related Art

The hair treatment formulations according to the invention include any formulations which enable the original color of the hair to be changed as described, for example, in the book entitled "Kosmetik" by Wilfried Umbach, Georg Thieme Verlag Stuttgart/New York, 1988, pages 284 to 291 and in the literature cited therein on page 297 under the heading "4.5 Mittel zur Farbänderung"; in "Cosmetics, Science and Technology", Editor Edward Sagarin, Interscience Publishers, Inc., New York and London, 1957, pages 479 to 530; in Karlheinz Schrader "Grundlagen und Rezepturen der Kosmetika", 2nd Improved and Extended Edition, Hüthig Buch Verlag, Heidelberg, 1989, pages 782 to 815; in "Hair Coloring", Rev. Prog. Coloration, Vol. 15, 52 et seq. (1985); and in J. F. Corbett "The Chemistry of Synthetic Dyes", Vol. 5, Edited by Venkataraman, Academic Press, New York and London, 1971.

Substantive dyes are normally processed individually or in the form of mixtures for hair treatment formulations in the form of hair tinting formulations, as also described in detail in the literature cited above.

Of particular significance for the coloring of hair are the so-called oxidation hair colorants which are formed by oxidative coupling of primary intermediates (for example p-phenylenediamines, p-aminophenols or p-diaminopyridines) with secondary intermediates (for example phenols, resorcinols, m-aminophenols, m-phenylenediamines, naphthols or pyrazolones). Under the boundary conditions encountered in practice (low coloring temperature, short coloring time), they give intensive colors with very good fastness values. Oxidation dyes also play an important part in the coloring of fur. Good oxidation hair colorants are expected to satisfy above all the following performance requirements: they must form the required color with sufficient intensity during the oxidative coupling reaction with the particular primary and secondary intermediates. The dyes formed, which should be absorbed readily and uniformly by the hair or fur, are expected to be generally stable and, in particular, fast to washing, light and perspiration and to be heat-resistant. In particular, they must not have any tendency to change the original color tone under the conditions under which the hair is normally worn. In addition, they are expected to be toxicologically and dermatologically safe.

However, for the oxidative coloring of hair, the oxidation dye precursors must be able to penetrate into the hair. To guarantee this, alkalis, preferably ammonia, are added to the hair colorants. The hair is always damaged during coloring both by the oxidizing agent which, although serving to couple the dye precursors, also destroys the melanin of the hair and by the alkali, more particularly by the ammonia. Accordingly, efforts are made to reduce the damage to the hair in another treatment step after oxidation coloring. This is done, for example, by treating the hair with a shampoo containing hair-care agents, rinses or conditioners.

DE 44 08 506 describes a hair colorant which contains phospholipid EFA [tri-(3-N,N-dimethyl-N-linolenamidopropyl-2-hydroxyammoniumpropyl)-phosphoric acid ester trichloride] as a hair-care agent. This particular hair-care agent improves the wet combability of the colored keratin fibers in relation to hair treated with known colorants. A positive effect is obtained during the coloring process, but only on the outer cuticle region. The internal structure of the hair is not improved.

DESCRIPTION OF THE INVENTION

Accordingly, the problem addressed by the present invention was to provide hair treatment formulations in the form of colorants for human hair based on substantive dyes and/or oxidation dye precursors containing hair-care agents which would not affect the condition of the hair during the actual coloring process or would even improve the structure of the hair from inside.

The problem addressed by the invention has been solved by the hair coloring formulations according to the invention, which are hair treatment formulations in the form of hair colorants for human hair based on substantive dyes and/or oxidation dye precursors containing typical cosmetic components and at least one hair-care agent, characterized in that they contain as the hair-care agent one or more compounds corresponding to general formula (I):

in which $R^1$ is a hydroxy group, a $(C_{1-3})$ alkoxy group or a group corresponding to general formula (II):

where $R^5$ is a hydroxy group, a $(CH_2)_3$—$NH_2$ group or a 4-hydroxyphenyl group and $R^6$ is hydrogen or a $(C_{1-3})$ alkyl group, $R^2$ is hydrogen or a $(C_{1-3})$ alkyl group, $R^3$ is a hydrogen or a methyl group and $R^4$ is a hydroxy group, a $(CH_2)_3$—$NH_2$ group or a 4-hydroxyphenyl or an $H_2PO_3$ group, and their physiologically compatible salts of inorganic and/or organic bases providing the compounds corresponding to general formulae (I) and (II) are present in the acid form and general formulae (I) and (II) include the D and L isomers and D/L mixtures (racemates). The hair-care agents of general formula (I) present in accordance with the invention are intended to penetrate into the hair to be colored and to be stable at pH values in the range from 2 to 12. In addition to improved combability and improved feel, they are intended above all to bring about clearly measurable and permanent structural stabilization of the hair, particularly where it is damaged.

The particular advantage of the present invention is that hair treated with the hair colorants described herein does not require the usual post-coloring treatment mentioned in the foregoing.

It is surprising that the hair colorants according to the invention demonstrably improve the structure of the hair during the actual coloring process.

Hair treatment formulations according to the invention may be present in the form of aqueous, powder-form, emulsified or dispersed hair colorants. Examples include solutions, cremes, emulsions, gels, foam aerosols or paste-like formulations.

In addition to at least one compound corresponding to general formula (I) in a quantity of 0.01 to 10% by weight, the hair colorants according to the invention may additionally contain tryptophane or another amino acid from the group consisting of glycine, alanine, valine, leucine, isoleucine, norleucine, phenyl alanine, arginine, histidine, proline, hydroxyproline, cystine, cystein, methionine, aspartic acid, glutamic acid and cysteic acid and/or mixtures thereof in quantities of 0.01 to 5% by weight.

In one particular embodiment, tryptophane may additionally be present in up to the same quantity by weight of the compounds corresponding to general formula (I).

Preferred hair-care agents of general formula (I) according to the invention are listed in Table I.

TABLE I

|  | $R^1$ | $R^2$ | $R^3$ | $R^4$ | $R^5$ | $R^6$ |
|---|---|---|---|---|---|---|
| Serine | OH | H | H | OH |  |  |
| Threonine | OH | H | $CH_3$ | OH |  |  |
| Tyrosine | OH | H | H | p-Hydroxyphenyl |  |  |
| Lysine | OH | H | H | —$(CH_2)_3$—$NH_2$ |  |  |
| Serine alkylester | $C_{1-3}$ alkoxy | H | H | OH |  |  |
| Threonine alkylester | $C_{1-3}$ alkoxy | H | $CH_3$ | OH |  |  |
| Phosphoserine | OH | H | H | $H_2PO_3$ |  |  |
| Phospho-threonine | OH | H | $CH_3$ | $H_2PO_3$ |  |  |
| Serine dimer | Formula (II) | H | H | OH | OH | H |

In addition to at least one hair-care agent corresponding to general formula (I), the hair colorants according to the invention may additionally contain one or more hair-care agents such as, for example, panthenol, tocopherol, wheat proteins, lecithins, keratin and silk hydrolyzates, phospholipids, ceramides, pseudoceramides, phytosterols. These additional hair-care agents may be present in hair colorants in quantities of 0.01 to 10% by weight.

Proteins, more particularly wheat proteins, are described inter alia in Römpp "Chemie Lexikon", 9th Edition, Vol. 5, pages 3650 to 3657 and Vol. 6 on pages 5029 to 5030. The use and effect of tocopherols is described inter alia in Römpp "Chemie Lexikon", 9th Edition, Vol. 6, pages 4637 to 4639. The structure and properties of phytosterols are described, for example, in "Parfümerie & Kosmetik", Vol. 75 (1994), pages 755 to 758. Lecithins and their properties are described, for example, by S. A. Riethmayer in "SÖFW", Vol. 121, (1995), pages 367 to 372. Ceramides and pseudoceramides are described inter alia in Römpp "Chemie Lexikon", 9th Edition, Vol. 1, page 623 with literature references.

Examples of substantive hair dyes for hair tinting formulations are 4-hydroxypropylamino-3-nitrophenol, HC Red No. 3, 4-amino-3-nitrophenol, 2-amino-6chloro-4-nitrophenol, HC Blue No. 2, HC Blue No. 12, HC Yellow No. 2 and HC Yellow No. 12, which may be present either individually or even in the form of mixtures with other substantive hair dyes known to the expert for the same purpose.

Examples of suitable primary intermediates (oxidation dye precursors) are primary aromatic or heteroaromatic amines containing another functional group in the p-position, such as p-phenylenediamine, p-toluylenediamine, p-aminophenol, 4-amino-m-cresol, 2-hydroxyethyl-1,4-diaminobenzene, 2,4,-5,6-tetraaminopyrimidine, 4,4'-diaminodiphenylamine and derivatives thereof, other compounds of the type mentioned which additionally contain one or more functional groups, such as OH groups, $NH_2$ groups, NHR groups, NRR groups, where R is an optionally substituted $C_{1-4}$ alkyl radical. Other primary intermediates known to the expert may also be used either individually or in the form of mixtures.

Secondary intermediates (oxidation dye precursors) such as, for example, α-naphthol, resorcinol, 4-chlororesorcinol, 2-methyl resorcinol, m-aminophenol, o-aminophenol, m-phenylenediamine, 1,5- and 2,7-dihydroxy-naphthalene, 4-amino-2-hydroxytoluene, 2,4-diaminophenoxyethanol, 3-amino-2,4-dichlorophenol, 2-amino-4-hydroxyethylaminoanisole, 2-amino-3-hydroxypyridine, 2,6-diaminopyridine and derivatives of these compounds may be used. Other secondary intermediates known to the expert may also be used either individually or in the form of mixtures.

In addition, the hair colorants based on oxidation dyes may optionally contain typical substantive hair dyes such as, for example, 4-hydroxypropyl-amino-3-nitrophenol, HC Red No. 3, 4-amino-3-nitrophenol, 2-amino-6-chloro-4-nitrophenol, HC Blue No. 2, HC Yellow No. 2, HC Blue No. 12, HC Yellow No. 12, HC Red No. 13, HC Red No. 3, HC Yellow No. 6, HC Red No. 10 and/or other substantive dyes known to the expert either individually or in the form of mixtures should this be necessary for obtaining certain shades of color. Substantive hair dyes also include synthetic dyes or extracted natural dyes such as, for example, indigo ([2,2'-biindoline]-3,3'-dione), maclurin (2,3',4,4',6-pentahydroxybenzophenone), brasilin (C.I. Natural Red 24), hematoxylin, alizarin (1,2-dihydroxyanthraquinone), juglone (5-hydroxy-1,4-naphthoquinone), curcumin (2,3,4, 6-tetrahydroxy-5H-benzocyclo6,8-heptadien-5-one), carminic acid (C.I. Natural Red 4) or chemically modified derivatives thereof.

Preferred embodiments of the invention for obtaining the shades of color indicated therein are set out in Table II, the preferred combinations of oxidation dye precursors and optionally substantive dyes being present in a quantity of 0.1 to 25% by weight and serine being present as the hair-care agent in a quantity of 0.5 to 2.5% by weight, based on the total quantity of cosmetic carrier. The figures in Table II represent the % by weight ranges of the oxidation dye precursors or substantive dyes which are identified by the following codes:

| Primary intermediates: | A-1 | p-toluylenediamine |
|---|---|---|
|  | A-2 | 4-amino-m-cresol |
| Secondary intermediates: | B-1 | resorcinol |
|  | B-2 | α-naphthol |
|  | B-3 | 2-methyl resorcinol |

-continued

|  |  |  |
|---|---|---|
|  | B-4 | m-aminophenol |
|  | B-5 | 4-chlororesorcinol |
|  | B-6 | 4-amino-2-hydroxytoluene |
|  | B-7 | 2-amino-4-hydroxyethylaminoanisole |
|  | B-8 | 2-amino-3-hydroxypyridine |
| Substantive dyes: | C-1 | 4-hydroxypropylamino-2-nitrophenol |
|  | C-2 | HC Red No. 3 |
|  | C-3 | 4-amino-3-nitrophenol |
|  | C-4 | 2-amino-6-chloro-4-nitrophenol |

| Shade/dye | A-1 | A-2 | B-1 | B-2 | B-3 | B-4 | B-5 | B-6 | B-7 | B-8 | C-1 | C-2 | C-3 | C-4 |
|---|---|---|---|---|---|---|---|---|---|---|---|---|---|---|
| Black | 4–10 | | 0.1–2 | | | 0.1–2 | | | 2–8 | | | | | |
| Dark brown | 3–8 | | 1–4 | | | 0.1–2 | | | 0.1–2 | 0.01–2 | | | | |
| Mid-brown | 0.3–3 | | 0.01–2 | | | 0.01–2 | | | 0.01–2 | | | | | |
| Light brown | 1–4 | | 0.01–2 | | 0.01–2 | 0.01–2 | | | | | | | | |
| Dark blond | 1–4 | | 0.01–2 | | 0.01–2 | 0.01–2 | | | | | | | | |
| Medium blond | 0.1–3 | | 0.01–2 | | 0.01–2 | 0.01–2 | | | | | | | | |
| Light blond | 0.1–3 | | 0.01–2 | | 0.01–2 | 0.01–2 | 0.01–2 | | | | | | | |
| Aubergine | 0.1–3 | | | | | | | 0.01–2 | | | 0.01–2 | 0.01–2 | | |
| Mocha brown | 0.05–4 | 0.01–2 | | 0.01–2 | | | | 0.05–2 | | | | 0.01–2 | | |
| Gold-mocha | 0.1–3 | | 0.01–2 | | 0.01–2 | 0.01–2 | | | | | | | | 0.01–2 |
| Brazil | 0.1–4 | 0.01–2 | | 0.01–2 | | 0.01–2 | | 0.02–2 | | | 0.02–2 | 0.01–2 | | |
| Red beech | 0.01–2 | 0.01–2 | 0.01–2 | | | | | 0.02–2 | | | 0.02–2 | 0.02–3 | | 0.01–2 |
| Dark gold-blond | 0.02–2 | 0.2–3 | 0.01–2 | | | | | 0.1–3 | | | 0.01–2 | | | 0.01–2 |
| Red-copper | 0.02–2 | 0.01–2 | | | | | | 0.01–2 | | | 0.01–2 | 0.01–2 | 0.01–2 | 0.01–2 |
| Hazelnut | 0.01–4 | 0.1–3 | 0.01–2 | | | | | 0.01–3 | | | 0.01–2 | | | 0.01–2 |
| Copper-brown | 0.01–2 | 0.01–2 | 0.01–2 | | | | | 0.01–2 | | | 0.01–2 | 0.01–2 | 0.01–2 | |
| Light copper | 0.01–2 | | | 0.01–1 | | | | 0.01–1 | | | | | | 0.01–2 |

The compositions of the hair colorants represent a mixture of the dye components with the additives typically used in such cosmetic formulations.

Typical additives in solutions, cremes, emulsions, gels or foam aerosols are, for example, solvents such as water, lower aliphatic alcohols, for example ethanol, propanol and isopropanol, glycols, glycerol and glycol ethers, such as propylene glycol, other wetting agents or emulsifiers from the classes of anionic, cationic, amphoteric or nonionic surfactants, such as fatty alcohol sulfates, alkyl sulfonates, alkyl benzenesulfonates, alkyl trimethyl ammonium salts, alkyl betaines, ethoxylated fatty alcohols, ethoxylated nonylphenols, fatty acid alkanolamides, ethoxylated fatty acid esters, and thickeners such as higher fatty alcohols, starch, cellulose derivatives, vaseline, paraffin oil and fatty acids.

The ingredients mentioned are used in the quantities normally employed for such purposes. For example, the wetting agents and emulsifiers may be present in concentrations of about 0.5 to 30% by weight while the thickeners may be present in the formulations in a quantity of about 0.1 to 25% by weight.

The hair colorants according to the invention may show a mildly acidic, neutral or alkaline reaction according to their composition. In particular, they have a pH value in the range from 6 to 12 which may be adjusted with ammonia, organic amines, such as monoethanolamine and triethanolamine, or even inorganic bases, such as sodium and potassium hydroxide. The preferred variant of the hair colorant has a pH value of 7 to 8 before the addition of aqueous oxidizing agent solutions and a pH value of 6.5 to 7.2 after mixing with an aqueous oxidizing agent solution in a ratio of 1:1 (w/w) to form a ready-to-use hair coloring gel.

For the oxidative coloring of hair, the colorants according to the invention, which contain a combination of at least one known primary intermediate with at least one secondary intermediate and the hair-care agents according to the invention, namely 0.01% by weight to 10% by weight of compounds corresponding to general formula (I), and optionally one or more other hair-care agents and optionally substantive dyes, are mixed with an oxidizing agent shortly before use and the resulting mixture is applied to the hair. Suitable oxidizing agents for developing the hair colorant are in the main hydrogen peroxide, for example in the form of a 6% aqueous solution, and adducts thereof with urea, melamine or sodium borate and mixtures of such hydrogen peroxide addition compounds with potassium peroxodisulfate. In principle, however, the color may also be oxidatively developed with atmospheric oxygen. The application temperatures are in the range from 15 to 40° C. After a contact time of about 30 minutes, the hair colorant is removed from the colored hair by rinsing. The hair may then be washed with a shampoo.

Besides improved combability, improved feel, increased shine and improved color levelling, additional advantageous properties in the form of measurable, permanent structural stabilization are surprisingly imparted by the haircare agent(s) of general formula (I) present in the hair colorant according to the invention.

The advantageous properties of human hair colored with the colorant according to the invention were determined by the following tests:

1. HP-DSC (High Pressure Differential Scanning Colorimetry)

Thermoanalytical studies are particularly suitable for characterizing two-phase systems which also include human hair as fiber keratins with their crystalline α-helix and amorphous matrix. On the one hand, glass transitions and aging behavior of the amorphous matrix can be investigated; on the other hand, the fusion behavior of the crystalline helical phase provides important information. Thermoanalytical studies were described for the first time in 1899 (W.

C. Roberts-Austen, Proc. Inst. Mech. Eng. London 1899, pages 35 et seq.). The first differential thermoanalyses (DTA) on protein fibers were carried out at the end of the fifties (F. Schwenker, J. H. Dusenbury, Text. Res. J. 1963, 30, pages 800 et seq.; W. D. Felix, M. A. McDowall, H. Eyring, ibid. 1963, 33, pages 465 et seq.). In the following years, various thermoanalytical measuring techniques, such as DTA, HP-DTA (high pressure DTA) and DSC (differential scanning calorimetry), were applied to keratin fibers (G. Ebert, F. H. Müller, Proc. Int. Wool Text. Res. Conf., Cirtel, Paris 1965, 4, pages 487 et seq.; G. Ebert, J. Wendorff, Kolloid-Zeitschrift und Zeitschrift für Polymere 1967, 216/217, pages 277 et seq.; M. Spei, R. Holzem, Colloid and Polymer Sci. 1987, 265, pages 965 et seq.; M. Spei, R. Holzem, Mell. Text. 1987, 68, pages 923 et seq.; A. R. Haly, J. W. Snaith, Text. Res. J. 1967, 37, pages 898 et seq.; J. S. Crighton, E. R. Hole, Proc. 7th Int. Wool Text. Res. Conf. 1985, Vol. 1, page 283; J. S. Crighton, W. M. Findon, Proc. 6th Int. Wool Text. Res. Conf., Pretoria 1980, Vol. V, pages 235 et seq.) in order, for example, to study the phenomenon of supercontraction, $\alpha$-$\beta$-phase transitions of the helices and denaturing processes. More recently, HP-DSC has been used to study keratin fibers, more particularly by the Deutsches Wollforschungsinstitut (German Wool Research Institute) in Aachen (F. J. Wortmann, H. Deutz, J. Appl. Polym. Sci. 1993, 48, pages 137 et seq.), because it is not attended by problems with pyrolytic effects, such as occur in conventional DSC, or by problems involving data acquisition and interpretation, such as occur in DTA. The DSC measurements are carried out on keratins which are accommodated with water in commercially available pressure-tight measuring capsules. On heating to temperatures above 100° C. in the encapsulated steel crucibles, a high water vapor pressure—from which the HP-DSC analysis derives—is built up in the keratin/water system. The major difference between HP-DSC thermograms of human hair and normal DSC thermograms is that the endothermal peaks which reproduce the transition point and enthalpy of transition are shifted by about 90° C. to lower temperatures. This stems from the fact that, after diffusing into the hair fibers, the water reduces the protein stability by weakening and breaking hydrogen bridge bonds and salt bonds and thus lowers the "gelatinization temperature" of the keratins. If only hydrogen bridges and salt bridges are broken by the supercontracting agent, such as water, the thermal effect is reversible (supercontraction). However, the process becomes irreversible when covalent bonds, such as disulfide bridges, are also broken. This occurs when human hair fibers are heated with water to beyond 150° C. in pressure-tight capsules. The irreversible transition, interpreted as the transition of the $\alpha$-helical regions in the proteins into a disordered state, results in endothermal peaks of which the position reproduces the transition point or even melting point while the area occupied by the peaks reproduces the enthalpy of transition or fusion.

Accordingly, it is possible by using dynamic differential calorimetry (DSC) to detect structural and chemical states and changes in fiber keratins, more particularly in human hair. In the case of human hair, the calorimetrically detectable processes can be recorded in the form of thermograms under precisely defined experimental conditions. The positions, structures and surface areas of the peaks can serve as indicators for influencing order/disorder transitions through changes in internal and/or external parameters produced, for example, by cosmetic treatment of the hair. In other words, information on the strength of or damage to human hair fibers can be derived from the position (transition point) and surface area (transition enthalpy) of the endothermal peaks recorded in the thermogram of human hair.

Extensive studies of the influence of the cystine content on the denaturing of the $\alpha$-helices in keratins have shown, for example, that the melting temperature (transition temperature) of the keratin increases linearly with the cystine content. The increased stability of the matrix region attributable to the relatively high degree of crosslinking of the high proportion of disulfide bridges in the matrix means that transition of the helices embedded in this matrix is made difficult and, accordingly, results in an increase in the melting temperature. Conversely, a reduction in the melting point and, above all, in the enthalpy of fusion can generally be observed in human hair treated by permanent waving or bleaching or coloring (H. Deutz, Doktorarbeit, RWTH Aachen 1993).

The hair-care agent(s) present in the hair colorants according to the invention, such as serine for example, penetrate(s) into the hair and, by virtue of its/their polar character, form additional hydrogen bridge and salt bonds in the matrix which in turn leads to increased stability against deformation and, hence, generally stabilizes the structure of the hair. This is evident in thermoanalytical studies of human hair treated with colorants according to the invention in the form of a shift of the transition or melting point of the human hair fibers to higher temperatures.

2. In addition, the structural stabilization produced by the hair colorants according to the invention is demonstrated by stress/strain measurements known to the expert on correspondingly colored human hair.

3. In addition, the structural stabilization produced by the hair colorants according to the invention is demonstrated by the so-called fatigue test. In this test, the human hair to be tested, after conditioning at 21° C./65% relative humidity, is individually clamped at its upper end to a platform and is provided at its lower end with a weight (30 to 40 g) so that it just rests on the floor. The platform moves vertically up and down so that the hair fibers are alternately placed under and relieved of load. Normally 100,000 cycles are carried out at a frequency of 1 cycle per second and the survival rate is determined. The stability of the fibers relative to one another is determined from this survival rate.

The invention is illustrated by the following Examples:

EXAMPLE 1

Oxidation Hair Color in Creme Form

| | |
|---|---|
| p-toluylenediamine | 1.85 g |
| m-aminophenol | 0.25 g |
| resorcinol | 0.65 g |
| 2-amino-4-(2-hydroxyethyl)-aminoanisole | 0.05 g |
| lauryl alcohol diglycol ether sulfate sodium salt (28% solution) | 5.00 g |
| cetyl alcohol | 10.00 g |
| myristyl alcohol | 6.00 g |
| oleic acid | 1.00 g |
| ammonia, 25% | 8.00 g |
| sodium dithionite | 0.40 g |
| L-serine | 2.00 g |
| water | to 100.00 g |

Shortly before use, the above-mentioned creme (50 g) is mixed as a hair colorant with 50 g of hydrogen peroxide solution (6% by weight). The mixture is left to act on 50% grey natural hair for 30 minutes at room temperature. The hair colorant is then rinsed out and the hair is shampooed and dried. It has acquired a uniform and full mid-brown color.

The fact that the hair-care agents according to the invention present in the hair colorant of Example 1 have a distinct and permanent structure-stabilizing effect on the hair, even during the coloring process, is apparent from the following investigations:

Damaged human hair tresses A and B were treated as follows:

A: Coloring with a 1:1 mixture of the coloring creme of Example 1 and hydrogen peroxide solution (6% by weight) for 30 minutes at room temperature, rinsing out and drying.

B: Coloring with a 1:1 mixture of the coloring creme of Example 1 and hydrogen peroxide solution (6% by weight) for 30 minutes at room temperature, but without addition of the L-serine rinsing out and drying.

The hair tresses A and B colored as described above were thermoanalyzed. Tress A was found to have a significantly higher melting point than tress B.

EXAMPLE 2

Hair Tinting Formulation

| | |
|---|---|
| HC Red No. 3 | 0.75 g |
| HC Yellow No. 2 | 0.20 g |
| 4-(3-hydroxypropylamino)-3-nitrophenol | 0.20 g |
| hydroxyethyl cellulose | 0.90 g |
| monoethanolamine lauryl sulfate | 5.00 g |
| cetyl alcohol | 1.00 g |
| D/L-serine | 1.00 g |
| L-tyrosine | 1.00 g |
| ethyl diglycol | 5.00 g |
| water | to 100.00 g |

Dark blond natural hair is treated with the solution of Example 2 for 30 minutes at 35° C., rinsed with water and dried. The hair has an intensive bright red tint.

The fact that the hair-care agents according to the invention present in the hair colorant of Example 2 have a distinct and permanent structure-stabilizing effect on the hair, even during the tinting process, is apparent from the following tests:

Damaged dark blond human hair tresses A and B were treated as follows:

A: Tinting with the solution of Example 2 for 30 minutes at 35° C., rinsing out and drying.

B: Tinting with the solution of Example 2 for 30 minutes at 35° C., but without addition of the D/L-serine and L-tyrosine, rinsing out and drying.

The hair tresses A and B tinted as described above were thermo-analyzed and subjected to stress/strain measurements.

Thermoanalysis showed that tress A had a significantly higher melting point than tress B. The stress/strain measurements revealed a significant improvement in the strength of tress A over tress B.

EXAMPLE 3

Oxidation Hair Color in Creme Form

| | |
|---|---|
| p-phenylenediamine | 0.75 g |
| resorcinol | 0.28 g |
| o-aminophenol | 0.01 g |
| m-aminophenol | 0.07 g |
| 2,6-diaminopyridine | 0.02 g |
| p-amino-o-cresol | 0.01 g |
| m-phenylenediamine | 0.01 g |
| 1,2-propylene glycol | 10.00 g |
| polyethylene glycol cocosamine | 7.00 g |
| isopropanol | 10.00 g |
| Cocamide DEA | 20.00 g |
| oleic acid | 8.00 g |
| sodium sulfite | 0.20 g |
| EDTA | 0.20 g |
| ammonia, 25% | 6.00 g |
| D/L-serine | 1.00 g |
| L-lysine | 1.00 g |
| water | to 100.00 g |

Just before use, 50 g of the above-mentioned creme are mixed with 50 g of hydrogen peroxide solution (6% by weight). The mixture is applied to 50% grey hair for 30 minutes at room temperature. The colorant is then rinsed out and the hair is shampooed and dried. It has acquired a uniform, light ash brown color.

The fact that the hair-care agents according to the invention present in the hair colorant of Example 3 have a distinct and permanent structure-stabilizing effect on the hair, even during the coloring process, is apparent from the following tests:

Damaged human hair tresses A and B were treated as follows:

A: Coloring with a 1:1 mixture of the coloring creme of Example 3 and hydrogen peroxide solution (6% by weight) for 30 minutes at room temperature, rinsing out and drying.

B: Coloring with a 1:1 mixture of the coloring creme of Example 3 and hydrogen peroxide solution (6% by weight) for 30 minutes at room temperature, but without addition of the D/L-serine and L-lysine rinsing out and drying.

The hair tresses A and B colored as described above were thermoanalyzed and subjected to stress/strain measurements.

Thermoanalysis showed that tress A had a significantly higher melting point than tress B. The stress/strain measurements revealed a significant improvement in strength for tress A over tress B.

EXAMPLE 4

Oxidation Hair Color in Gel Form

| | |
|---|---|
| p-toluylenediamine | 0.20 g |
| 4-amino-m-cresol | 1.00 g |
| resorcinol | 0.09 g |
| 4-amino-2-hydroxytoluene | 1.00 g |
| 2-amino-3-hydroxypyridine | 0.10 g |
| 2-amino-6-chloro-4-nitrophenol | 0.05 g |
| polyacrylic acid, ammonium salt, 10% | 15.00 g |
| cetostearyl alcohol | 8.00 g |
| cetostearyl sulfate, sodium salt | 1.00 g |

-continued

| | |
|---|---|
| PEG 40 castor oil | 1.00 g |
| disodium laureth-5-sulfosuccinate (lanolin sulfosuccinate) | 4.00 g |
| sodium sulfite | 0.20 g |
| monoethanolamine | 0.30 g |
| L-lysine | 2.00 g |
| water | to 100.00 g |

Shortly before use, 50 g of the gel mentioned above are mixed with 50 g of hydrogen peroxide solution (3% by weight) and the resulting mixture was uniformly applied to medium blond natural hair. After a contact time of 30 minutes at room temperature, the hair coloring gel is rinsed out and the hair is shampooed and dried. It has acquired a uniform hazelnut brown color.

The fact that the hair-care agents according to the invention present in the hair colorant of Example 4 have a distinct and permanent structure-stabilizing effect on the hair, even during the coloring process, is apparent from the following tests:

Damaged human hair tresses A and B were treated as follows:

A: Coloring with a 1:1 mixture of the coloring gel of Example 4 and hydrogen peroxide solution (3% by weight) for 30 minutes at room temperature, rinsing out and drying.

B: Coloring with a 1:1 mixture of the coloring gel of Example 4 and hydrogen peroxide solution (3% by weight) for 30 minutes at room temperature, but without addition of the L-lysine, rinsing out and drying.

The hair tresses A and B colored as described above were thermoanalyzed. Tress A was found to have a significantly higher melting point than tress B.

EXAMPLE 5

Oxidation Hair Color in Creme Form

| | |
|---|---|
| p-toluylenediamine | 0.50 g |
| resorcinol | 0.15 g |
| 2-methyl resorcinol | 0.06 g |
| m-aminophenol | 0.50 g |
| polyacrylic acid, ammonium salt, 1% | 17.00 g |
| cocamidopropyl betaine | 18.00 g |
| EDTA | 0.30 g |
| cetyl alcohol | 2.00 g |
| fatty alcohol polyglycol ether | 7.00 g |
| myristyl alcohol | 1.50 g |
| KOH, 50% | 0.50 g |
| sodium dithionite | 0.30 g |
| D/L-serine | 0.50 g |
| L-threonine | 0.59 g |
| water | to 100.00 g |

Shortly before use, 35 g of the gel mentioned above were mixed with 70 g of hydrogen peroxide solution (1.5% by weight) and, after application, the resulting mixture was left on the hair for 30 minutes at room temperature. The hair coloring gel is then rinsed out and the hair is shampooed and dried. It has acquired a medium blond color.

The fact that the hair-care agents according to the invention present in the hair colorant of Example 5 have a distinct and permanent structure-stabilizing effect on the hair, even during the coloring process, is apparent from the following tests:

Slightly damaged human hair tresses A and B were treated as follows:

A: Coloring with a 1:2 mixture of the coloring gel of Example 5 and hydrogen peroxide solution (1.5% by weight) for 30 minutes at room temperature, rinsing out and drying.

B: Coloring with a 1:2 mixture of the coloring gel of Example 5 and hydrogen peroxide solution (1.5% by weight) for 30 minutes at room temperature, but without addition of the D/L-serine and L-threonine, rinsing out and drying.

The hair tresses A and B colored as described above were thermoanalyzed and subjected to stress/strain measurements.

Thermoanalysis showed that tress A had a significantly higher melting point than tress B. The stress/strain measurements revealed a significant improvement in strength for tress A over tress B.

EXAMPLE 6

Oxidation Hair Color in Gel Form

| | |
|---|---|
| p-toluylenediamine | 0.85 g |
| resorcinol | 0.30 g |
| 2-methyl resorcinol | 0.08 g |
| m-aminophenol | 0.07 g |
| polyacrylic acid, ammonium salt 10% | 15.00 g |
| cetostearyl alcohol | 8.00 g |
| cetostearyl sulfate, sodium salt | 1.00 g |
| PEG 40 castor oil | 1.00 g |
| disodium laureth-5-sulfosuccinate (lanolin sulfosuccinate) | 4.00 g |
| sodium sulfite | 0.20 g |
| monoethanolamine | 0.30 g |
| D/L-serine | 2.00 g |
| water | to 100.00 g |

Just before use, 50 g of the gel mentioned above are mixed with 50 g of hydrogen peroxide solution (1.5% by weight) and the resulting mixture is uniformly applied to 50% grey natural hair. After a contact time of 30 minutes at room temperature, the hair coloring gel is rinsed out and the hair is shampooed and dried. It has acquired a uniform dark blond color.

The fact that the hair-care agents according to the invention present in the hair colorant of Example 6 have a distinct and permanent structure-stabilizing effect on the hair, even during the coloring process, is apparent from the following tests:

Slightly damaged human tresses A and B were treated as follows:

A: Coloring with a 1:1 mixture of the coloring gel of Example 6 and hydrogen peroxide solution (1.5% by weight) for 30 minutes at room temperature, rinsing out and drying.

B: Coloring with a 1:1 mixture of the coloring gel of Example 6 and hydrogen peroxide solution (1.5% by weight) for 30 minutes at room temperature, but without addition of the D/L-serine, rinsing out and drying.

The hair tresses A and B colored as described above were thermoanalyzed and subjected to stress/strain measurements and fatigue tests.

Thermoanalysis showed that tress A had a significantly higher melting point than tress B. The stress/strain measurements revealed a significant improvement in strength for tress A over tress B. The fatigue test revealed a significantly higher survival rate for tress A compared with tress B.

EXAMPLE 7

Oxidation Hair Dye in Gel Form

| | |
|---|---|
| p-toluylenediamine | 8.55 g |
| resorcinol | 1.00 g |
| m-aminophenol | 0.20 g |
| 2-amino-4-(2-hydroxyethyl)-aminoanisole | 6.07 g |
| polyacrylic acid, ammonium salt 10% | 15.00 g |
| cetostearyl alcohol | 8.00 g |
| cetostearyl sulfate, sodium salt | 1.00 g |
| PEG 40 castor oil | 1.00 g |
| disodium laureth-5-sulfosuccinate (lanolin sulfosuccinate) | 4.00 g |
| sodium sulfite | 0.20 g |
| monoethanolamine | 0.30 g |
| L-serine | 1.00 g |
| L-tryptophane | 1.00 g |
| water | to 100.00 g |

Just before use, 50 g of the gel mentioned above are mixed with 50 g of hydrogen peroxide solution (3% by weight) and the resulting mixture is uniformly applied to 50% grey natural hair. After a contact time of 30 minutes at room temperature, the hair coloring gel is rinsed out and the hair is shampooed and dried. It has acquired a uniform deep black color.

The fact that the hair-care agents present in the hair colorant of Example 7 have a distinct and permanent structure-stabilizing effect on the hair, even during the coloring process, is apparent from the following tests:

Damaged human hair tresses A and B were treated as follows:

A: Coloring with a 1:1 mixture of the coloring gel of Example 7 and hydrogen peroxide solution (3% by weight) for 30 minutes at room temperature, rinsing out and drying.

B: coloring with a 1:1 mixture of the coloring gel of Example 7 and hydrogen peroxide solution (3% by weight) for 30 minutes at room temperature, but without addition of the L-serine and L-tryptophane, rinsing out and drying.

The hair tresses A and B colored as described above were thermoanalyzed. Tress A was found to have a significantly higher melting point than tress B.

EXAMPLE 8

Oxidation Hair Dye in Creme Form

| | |
|---|---|
| p-toluylenediamine | 0.18 g |
| 2-ethyl resorcinol | 0.09 g |
| 2-amino-3-hydroxypyridine | 0.03 g |
| 2-amino-4-chloro-4-nitrophenol | 0.10 g |
| polyacrylic acid, ammonium salt, 1% | 17.00 g |
| cocamidopropyl betaine | 18.00 g |
| EDTA | 0.30 g |
| cetyl alcohol | 2.00 g |
| fatty alcohol polyglycol ether | 7.00 g |
| myristyl alcohol | 1.50 g |
| KOH, 50% | 0.50 g |
| sodium dithionite | 0.30 g |
| L-lysine | 1.00 g |
| L-threonine | 0.50 g |
| water | to 100.00 g |

Shortly before use, 35 g of the gel mentioned above are mixed with 70 g of hydrogen peroxide solution (1.5% by weight) and, after application, the resulting mixture is left on the light blond grey hair for 30 minutes at room temperature. The hair coloring gel is then rinsed out and the hair is shampooed and dried. It has acquired a light copper color.

The fact that the hair-care agents according to the invention present in the hair colorant of Example 8 have a distinct and permanent structure-stabilizing effect on the hair, even during the coloring process, is apparent from the following tests:

Damaged human hair tresses A and B were treated as follows:

A: Coloring with a 1:2 mixture of the coloring gel of Example 8 and hydrogen peroxide solution (1.5% by weight) for 30 minutes at room temperature, rinsing out and drying.

B: Coloring with a 1:2 mixture of the coloring gel of Example 8 and hydrogen peroxide solution (1.5% by weight) for 30 minutes at room temperature, but without addition of the L-lysine and L-threonine, rinsing out and drying.

The hair tresses A and B colored as described above were thermoanalyzed. Tress A was found to have a significantly higher melting point than tress B.

EXAMPLE 9

Oxidation Hair Dye in Gel Form

| | |
|---|---|
| p-toluylenediamine | 0.91 g |
| 4-amino-2-hydroxytoluene | 0.40 g |
| 4-amino-2-hydroxypyridine | 0.08 g |
| 4-hydroxypropylamino-2-nitrophenol | 0.25 g |
| polyacrylic acid, ammonium salt, 10% | 15.00 g |
| cetostearyl alcohol | 8.00 g |
| cetostearyl sulfate, sodium salt | 1.00 g |
| PEG 40 castor oil | 1.00 g |
| disodium laureth-5-sulfosuccinate (lanolin sulfosuccinate) | 4.00 g |
| sodium sulfite | 0.20 g |
| monoethanolamine | 0.30 g |
| L-serine | 1.00 g |
| water | to 100.00 g |

Shortly before use, 50 g of the gel mentioned above are mixed with 50 g of hydrogen peroxide solution (3% by weight) and the resulting mixture is uniformly applied to 50% grey mid-brown natural hair. After a contact time of 30 minutes at room temperature, the hair coloring gel is rinsed out and the hair is shampooed and dried. It has acquired a uniform aubergine color.

The fact that the hair-care agents according to the invention present in the hair colorant of Example 9 have a distinct and permanent structure-stabilizing effect on the hair, even during the coloring process, is apparent from the following tests:

Damaged human hair tresses A and B were treated as follows:

A: Coloring with a 1:1 mixture of the coloring gel of Example 9 and hydrogen peroxide solution (3% by weight) for 30 minutes at room temperature, rinsing out and drying.

B: Coloring with a 1:1 mixture of the coloring gel of Example 9 and hydrogen peroxide solution (3% by weight) for 30 minutes at room temperature, but without addition of the L-serine, rinsing out and drying.

The hair tresses A and B colored as described above were thermoanalyzed. Tress A was found to have a significantly higher melting point than tress B.

EXAMPLE 10

Oxidation Hair Color in Gel Form

| | |
|---|---|
| P-toluylenediamine | 0.85 g |
| resorcinol | 0.30 g |
| 2-methyl resorcinol | 0.08 g |
| m-aminophenol | 0.07 g |
| polyacrylic acid, ammonium salt, 10% | 15.00 g |
| cetostearyl alcohol | 8.00 g |
| cetostearyl sulfate, sodium salt | 1.00 g |
| PEG 40 castor oil | 1.00 g |
| disodium laureth-5-sulfosuccinate (lanolin sulfosuccinate) | 4.00 g |
| sodium sulfite | 0.20 g |
| monoethanolamine | 0.30 g |
| L-serine | 1.00 g |
| L-histidine | 0.50 g |
| water | to 100.00 g |

Shortly before use, 50 g of the gel mentioned above are mixed with 50 g of hydrogen peroxide solution (1.5% by weight) and the resulting mixture is uniformly applied to 50% grey natural hair. After a contact time of 30 minutes at room temperature, the hair coloring gel is rinsed out and the hair is shampooed and dried. It has acquired a uniform dark blond color.

The fact that the active substances present in the hair colorant of Example 10 have a distinct and permanent structure-stabilizing effect on the hair, even during the coloring process, is apparent from the following tests:

Damaged human hair tresses A and B were treated as follows:

A: Coloring with a 1:1 mixture of the coloring gel of Example 10 and hydrogen peroxide solution (1.5% by weight) for 30 minutes at room temperature, rinsing out and drying.

B: Coloring with a 1:1 mixture of the coloring gel of Example 10 and hydrogen peroxide solution (1.5% by weight) for 30 minutes at room temperature, but without addition of the L-serine and L-histidine, rinsing out and drying.

The hair tresses A and B colored as described above were thermoanalyzed and subjected to stress/strain measurements.

Thermoanalysis showed that tress A had a significantly higher melting point than tress B. The stress/strain measurements revealed a significant improvement in strength for tress A over tress B.

EXAMPLES 11 to 15

Examples 11 to 15 correspond to Examples 1 to 5, except that the hair-care agents mentioned in those Examples were replaced by 1% by weight of D/L-serine, 2% by weight of phospholipid EFA (a liquid safflower-derived biomimetic phospholipid complex from Mona Industries Inc.) and 2% by weight of panthenol as a combination of hair-care agents. Thermoanalysis of human hair treated with the colorants according to the invention containing serine, phospholipid EFA and panthenol as a combination of hair-care agents by comparison with hair treated with corresponding colorants without this combination revealed a clear structure-stabilizing effect for the colorants according to the invention and, in addition, a stronger structure-stabilizing effect than corresponding colorants containing only one or two of the hair-care agents of the combination according to the invention.

EXAMPLES 16 to 20

Examples 16 to 20 correspond to Examples 6 to 10 except that the hair-care agents mentioned in those Examples were replaced by 1% of serine, 2% by weight of keratin hydrolyzate and 4% by weight of soya lecithin as a combination of hair-care agents. Thermoanalysis of human hair treated with the colorants according to the invention containing serine, keratin hydrolyzate and soya lecithin as a combination of hair-care agents by comparison with hair treated with corresponding colorants without this combination revealed a clear structure-stabilizing effect for the colorants according to the invention and, in addition, a stronger structure-stabilizing effect than corresponding colorants containing only one or two of the hair-care agents present in the combination according to the invention.

In another embodiment of the present invention, the developer lotion (oxidizing agent solution) contains hair-care agents either individually or in combination, the hair-care agents or combinations thereof being the same as or different from those in the carrier (coloring creme, gel or powder). This embodiment is illustrated by the following Examples.

EXAMPLE 21 to 40

The procedure was as described in Examples 1 and 3 to 20 except that the hydrogen peroxide solution (developer lotion) contained an addition of a combination of 1% by weight of serine, 2% by weight of phospholipid EFA and 2% by weight of panthenol. Comparison of human hair colored with the colorants of Examples 21 to 40 with human hair treated with the corresponding colorant without the hair-care agents according to the invention or combinations thereof clearly shows a structure-improving effect and a better hair-care effect.

EXAMPLES 41 to 60

The procedure was as in Examples 1 and 3 to 20, except that the hydrogen peroxide solution (developer lotion) contained an addition of a combination of 1% by weight of serine, 2% by weight of keratin hydrolyzate and 4% by weight of soya lecithin. Comparative investigations revealed a distinct structure-improving effect and a better hair-care effect for the colorants according to the invention containing the combination of hair-care agents.

EXAMPLES 61 to 70

The procedure was as in Examples 1 to 10, except that the hair-care agents used in those Examples were replaced by 2% by weight of phosphoserine as the hair-care agent. Comparative investigations revealed a distinctly better hair-care effect and structure-stabilizing effect for the hair colorants containing phosphoserine as the hair-care agent by comparison with the corresponding hair colorants containing no phosphoserine.

EXAMPLES 71 to 80

The procedure was as in Examples 1 to 10 except that the hair-care agents used there were replaced by 2% by weight of serine methyl ester as the hair-care agent. Comparative investigations revealed that the hair colorants containing serine methyl ester as the hair-care agent had a distinctly better hair-care and structure-stabilizing effect than the corresponding hair colorants without any serine methyl ester.

Comparative Measurements to Illustrate the Degree of Invention

A few comparative investigations are reported by way of example in the following as proof of the degree of invention.

The method of thermal differential calorimetry (DSC) explained on pages 10 to 12 of the general description was used for these investigations.

Figure 1:
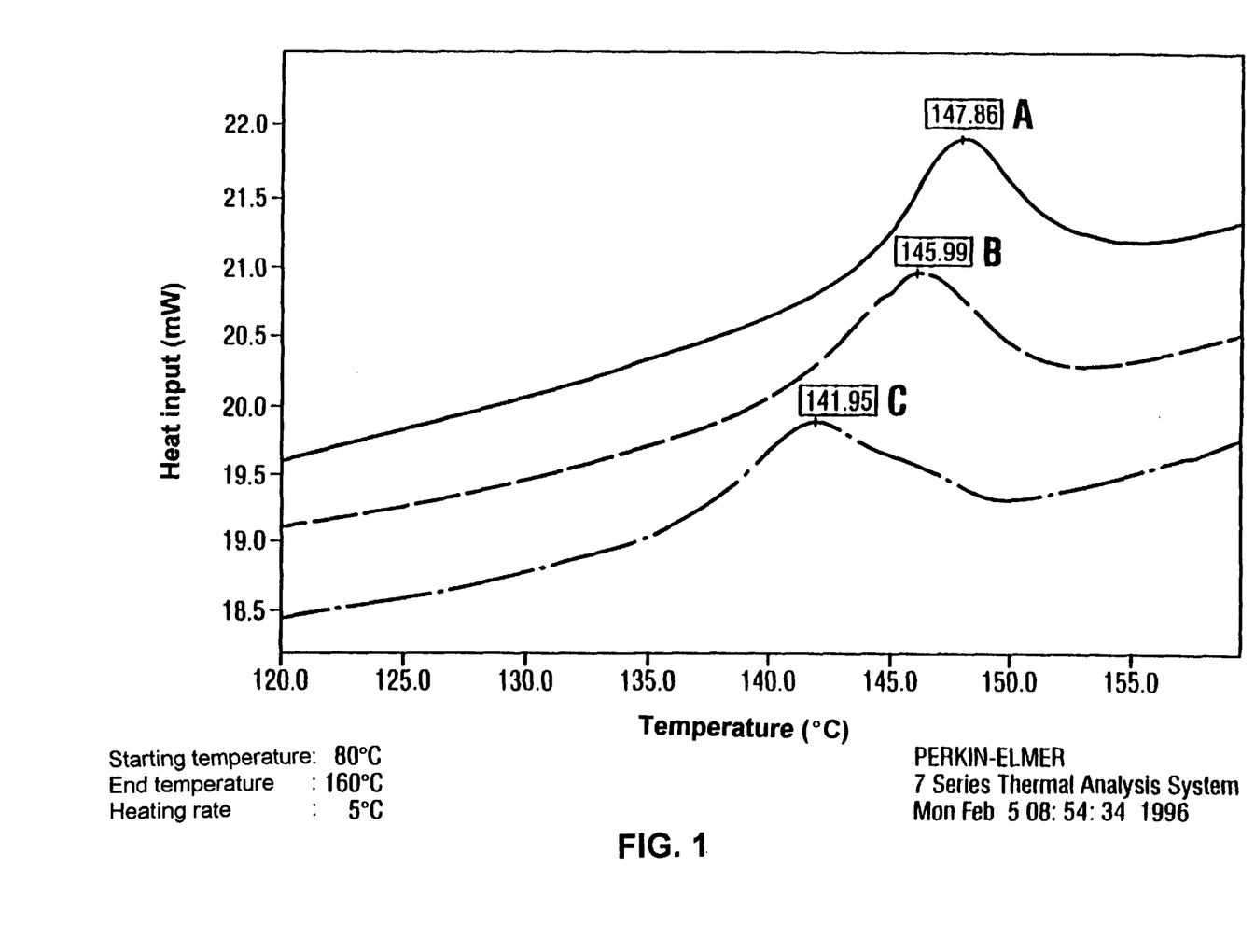

FIG. 1 shows the corresponding detail (melting peak) of the thermogram of an untreated damaged human hair tress (curve A) by comparison with the thermogram details of the same damaged human hair sample, but colored with the hair colorant in creme form without an added hair-care agent (curve C) and with a hair-colorant in creme form containing 2% by weight of L-serine as a hair-care agent (curve B). The peak maxima shown correspond to the particular melting point of the keratin which correlates directly with the structural stability of the hair. It can clearly be seen that, by coloring the damaged human hair with the hair colorant without the hair-care agent according to the invention, the melting point is reduced from 148° C. to 142° C. whereas, by coloring the damaged human hair with the hair colorant according to the invention containing 2% by weight of L-serine as hair-care agent, the melting point undergoes a far smaller reduction to 146° C. Accordingly, by adding the hair-care agent according to the invention to the hair colorant, the hair clearly suffers less damage during the coloring process.

Figure 2:
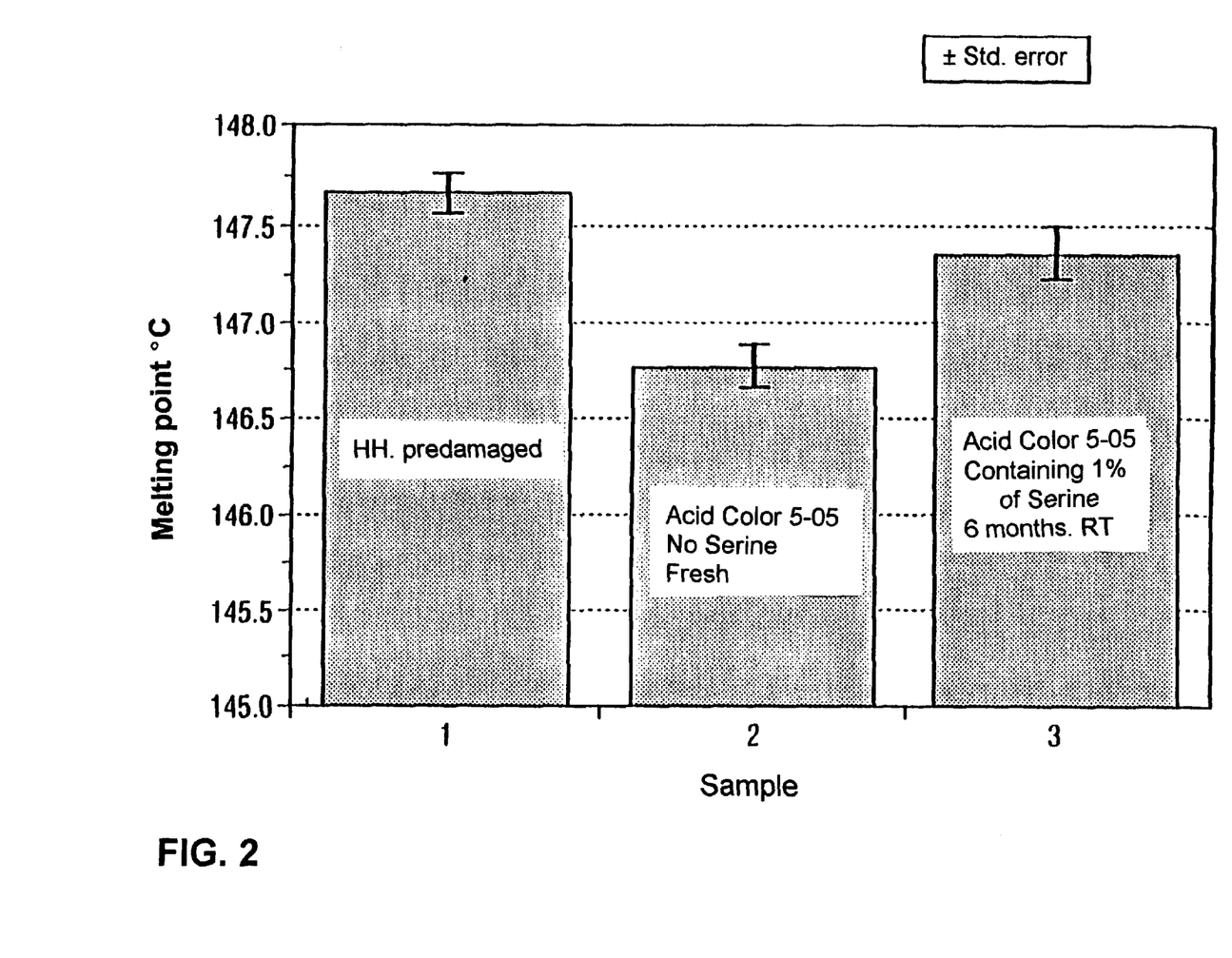

FIG. 2 shows the statistical evaluation of comparative thermoanalytical investigations of damaged human hair gel prepared by 1:2 mixing of the corresponding color base and 1.5% hydrogen peroxide solution. It can clearly be seen from the diagram (FIG. 3) that, in this test, the reduction in the melting point of the keratin produced by the coloring process, i.e. the structure-destabilizing effect on the keratin, is significantly reduced by the addition of D/L-serine to the hair colorant, preferably in a concentration of 1% by weight.

The following further comparative tests are also intended to demonstrate the degree of invention:

Human hair tresses were treated with the hair colorants of Example 10 containing the compounds mentioned in Table III as hair-care agents in a concentration of 2% by weight instead of the hair-care agents of that Example. The colored hair tresses were then thermoanalyzed. The increases in the melting point of keratin produced by the hair-care agents or combinations thereof (Δ peak in ° C.) are shown in Table III, the hair tresses treated with the colorant containing no hair-care agents serving as zero reference (test 1). It can clearly be seen that, in these tests, a structure-stabilizing effect is obtained by addition of the hair-care agents according to the invention.

TABLE III

| Tests | 1 | 2 | 3 | 4 | 5 | 6 | 7 | 8 | 9 | 10 | 11 |
|---|---|---|---|---|---|---|---|---|---|---|---|
| D/L-serine |  | X |  |  | X |  | X |  |  |  |  |
| L-serine |  |  | X |  |  |  |  |  |  | X | X |
| L-threonine |  |  |  |  |  |  |  |  |  |  |  |
| L-lysine HCl |  |  |  | X | X |  |  |  |  |  |  |
| L-tyrosine |  |  |  |  |  |  |  |  |  |  |  |
| D/L-tryptophane |  |  |  |  |  | X | X |  |  |  |  |
| D/L-phosphoserine |  |  |  |  |  |  |  | X | X |  |  |
| Serine methyl ester HCl |  |  |  |  |  |  |  |  |  | X | X |
| Δ Peak in ° C. | 0 | +0.6 | +0.8 | +0.4 | +0.4 | +0.3 | +0.5 | +1.5 | +1.7 | +1.1 | 1.4 | denoted here as "predamaged" (sample 1) which was treated on the one hand with a gel-form hair colorant without the hair-care agent according to the invention (sample 2) and, on the other hand, with the corresponding hair colorant containing 1% by weight of D/L-serine as the hair-care agent according to the invention (sample 3). It is clear from the diagram that, by adding 1% by weight of D/L-serine as hair-care agent to hair colorants, the melting point undergoes a smaller reduction during the coloring of human hair than without the addition of a corresponding hair-care agent, i.e. the hair suffers far less damage. In addition, the results were obtained with a freshly prepared hair colorant containing no hair-care agent against a hair colorant containing 1% by weight of D/L-serine as hair-care agent which had been stored for 6 months at room temperature, which proves that the hair-care agent in the formulation is totally stable.

Figure 3:
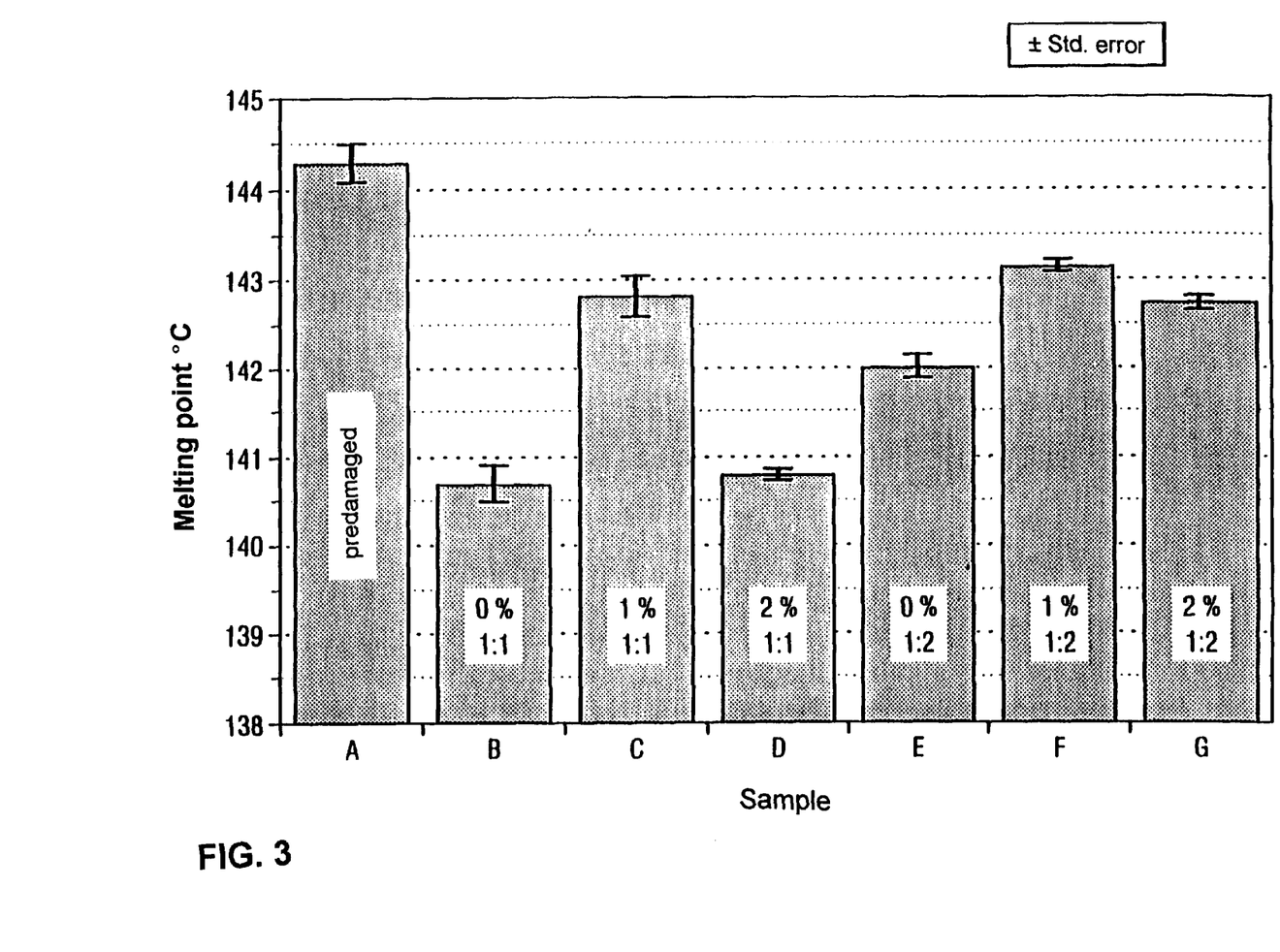

FIG. 3 shows the results of comparative thermoanalytical investigations in which damaged human hair (sample A), denoted here as "pre-damaged", was investigated in conjunction with the same human hair treated with a gel-form colorant containing no hair-care agent according to the invention (samples B and E) and with the corresponding hair colorant containing 1 or even 2% by weight of D/L-serine as hair-care agent (samples C and F and D and G). Samples B, C and D were obtained by treatment of damaged hair (sample A) with the coloring gel prepared by 1:1 mixing of the corresponding color base and 1.5% hydrogen peroxide solution whereas samples E, F and G had been obtained by treatment of the damaged hair (sample A) with the coloring Human hair tresses were treated with the hair colorants of Examples 11 to 15 containing the hair-care agents individually and in the possible two-component combinations rather than in the full three-component combination and were then thermoanalyzed. The resulting reductions in the melting point of keratin (Δ peak in ° C.), based on the coloring of hair with hair colorants without the hair-care agents according to the invention as zero reference (test 1), are shown in Table IV and make it clear that, in this series of tests, the addition of the hair-care agent phospholipid EFA or panthenol alone has only a slight structure-stabilizing effect on the hair. However, comparison of tests 2 and 3 with test 5 and of tests 2, 3 and 4 with test 8 of this series makes it clear that a strong structure-stabilizing effect can be observed by virtue of a surprising synergistic effect of the hair-care agents:

TABLE IV

| Tests | 1 | 2 | 3 | 4 | 5 | 6 | 7 | 8 |
|---|---|---|---|---|---|---|---|---|
| Phospholipid EFA* |  | X |  |  | X | X |  | X |
| D/L-serine |  |  | X |  | X |  | X | X |
| Panthenol |  |  |  | X |  | X | X | X |
| Δ Peak in ° C. | 0 | +0.1 | +0.6 | +0.3 | +1.1 | +0.3 | +0.8 | +1.2 |

*INCI: LINOLEAMIDOPROPYL PG-DIMONIUM-CHLORIDE-PHOSPHATE (Mona)

Human hair tresses were treated with the hair colorants of Examples 16 to 20 containing the hair-care agents individually and in the possible two-component combinations rather than in the full three-component combination and were then thermoanalyzed. The resulting reductions in the melting point of keratin (Δ peak in ° C.), based on the coloring of hair with hair colorants without the hair-care agents according to the invention (zero reference), are shown in Table V:

TABLE V

| Tests | 1 | 2 | 3 | 4 | 5 | 6 | 7 | 8 |
|---|---|---|---|---|---|---|---|---|
| Keratin hydrolyzate* | | X | | | X | X | | X |
| Soya lecithin** | | | X | | X | | X | X |
| D/L-serine | | | | X | | X | X | X |
| Δ Peak in ° C. | 0 | +0.7 | −0.2 | +0.6 | +0.9 | +1.1 | +0.8 | +1.5 |

*INCI: HYDROLYZED KERATIN, Trade name: PROMOIS WK (Seiwa Kasei)
**INCI: DIHYDROXYETHYL SOJAMIN DIOLEATE, Trade name: Lowenol S 216 (Lowenstein)

Accordingly, a structure-stabilizing effect is achieved in this series of tests by the addition of the hair-care agents alone (except for soya lecithin). Comparison of tests 2 and 3 with test 5 and of tests 3 and 4 with test 7 reveals surprising synergistic effects of the two-component combination. Comparison of test 8 with tests 1 to 7 of this series shows the even greater synergistic effect of all three hair-care agents together.

We claim:

1. A hair treatment formulation for coloring human hair comprising a substantive dye, oxidation dye precursors, or mixtures thereof and 0.1% to 10% by weight of a hair care agent comprising a compound of the formula (I):

wherein $R^1$ is a group of the formula (II):

wherein $R^2$ and $R^3$ are hydrogen, $R^4$ and $R^5$ are hydroxy, and $R^6$ is hydrogen, including physiologically compatible salts of organic or inorganic bases of said compounds of formula (I).

2. A hair treatment formulation according to claim 1, further comprising 0.01% to 10% by weight serine, 0.1% to 5% by weight keratin hydrozylate, and 0.1% to 8% by weight soya lecithin.

* * * * *

UNITED STATES PATENT AND TRADEMARK OFFICE
CERTIFICATE OF CORRECTION

PATENT NO. : 6,129,770
DATED : October 10, 2000
INVENTOR(S) : Deutz et al.

It is certified that error appears in the above-identified patent and that said Letters Patent is hereby corrected as shown below:

Title page,
Item [73], Assignee, delete "Henkel Kommanditgesellschaft auf Aktien (KGaA), Duesseldorf, Germany, and insert therefor -- Hans Schwarzkopf GmbH, Hamburg, Germany --.
Item [57], ABSTRACT, delete "$CH_2$)" and insert therefor -- ($CH_2$) --.

Signed and Sealed this

Twelfth Day of October, 2004

JON W. DUDAS
*Director of the United States Patent and Trademark Office*